United States Patent [19]

DeZeeuw et al.

[11] 4,407,953
[45] Oct. 4, 1983

[54] FERMENTATION PROCESS FOR PRODUCTION OF ALPHA-ISOPROPYLMALIC ACID

[75] Inventors: John R. DeZeeuw, Stonington; Irene Stasko, Groton, both of Conn.

[73] Assignee: Pfizer Inc., New York, N.Y.

[21] Appl. No.: 381,595

[22] Filed: May 24, 1982

[51] Int. Cl.$^3$ .................. C12P 7/00; C12N 15/00; C12N 1/14; C12R 1/645
[52] U.S. Cl. .................. 435/145; 435/172; 435/255; 435/923
[58] Field of Search ............... 435/142, 143, 145, 172, 435/254, 255, 248, 923; 23/297

[56] References Cited

U.S. PATENT DOCUMENTS 3,843,466 10/1974 Akabori et al. ............ 435/142
3,986,933 10/1976 Maldonado et al. ............ 435/923

OTHER PUBLICATIONS

Kirk-Othmer, *Encyclopedia of Chemical Technology*, 3rd Edition; John Wiley and Sons (1981); pp. 903–907.
Calvo et al., "The Absolute Configuration of α-Hydroxy-β-Carboxyisocaproic Acid (3-Isopropylmalic Acid), an Intermediate in Levcine Biosynthesis", Biochemistry, 3 (1964), pp. 2024–2027.
Sai, Agr. Biol. Chem. 32, 522–524 (1968).

*Primary Examiner*—Thomas G. Wiseman
*Assistant Examiner*—Deborah A. Grossman
*Attorney, Agent, or Firm*—Charles J. Knuth; Albert E. Frost; Peter C. Richardson

[57] ABSTRACT

A process for producing alpha-isopropylmalic acid by aerobically fermenting a new strain of *Yarrowia lipolytica* and for recovering said acid from a fermentation medium.

8 Claims, No Drawings

FERMENTATION PROCESS FOR PRODUCTION OF ALPHA-ISOPROPYLMALIC ACID

BACKGROUND OF THE INVENTION

This invention relates to a process for producing alpha-isopropylmalic acid by fermentation. More particularly, it relates to a process for producing alpha-isopropylmalic acid by cultivating a new strain of the yeast *Yarrowia lipolytica* in an aqueous medium containing assimilable sources of carbon, nitrogen, L-leucine and inorganic salts under submerged aerobic conditions and to an improved process for recovering alpha-isopropylmalic acid from fermentation broth.

Isolation of alpha-isopropylmalic acid from culture medium of a leucine-requiring mutant of *Neurospora crassa* is reported by Burns et al., Biochemistry 2, 1053 (1963) and by Calvo et al., Biochemistry 3, 2024 (1964).

The accumulation of alpha-isopropylmalic acid [beta-carboxy-beta-hydroxyisocaproic acid or S(−)-2-hydroxy-2-(1-methylethyl)butanedioic acid] as a metabolic product of leucine-requiring mutants (auxotrophs) of *Saccharomyces cerevisiae* and its isolation from fermentation broths containing it by acidification and ether extraction of the broth is reported by Sai, Agr. Biol. Chem. 32, 522–4, (1968).

A partial bibliography of the discovery of alpha-isopropylmalic acid as a precursor for leucine biosynthesis in *Torulopsis utilis*, as a metabolic product of some strains of bacteria and molds which requires leucine for growth, and its enzymatic formation in cell-free preparations of baker's yeast is presented by Sai (loc. cit.).

French Pat. No. 2,417,548, granted Oct. 19, 1979, describes preparation of alpha-isopropylmalic acid by aerobic fermentation of *Brevibacterium* or Corynebacterium species.

Fultz et al., J. Bacteriol. 142, 513–520 (1980) report construction of two *Salmonella typhimurium* strains by a series of P22-mediated transductions. One strain accumulated and excreted alpha-isopropylmalic acid exclusively, the amount of said acid isolatable from culture media thereof being more than five times that produced by *Neurospora crassa*. The second accumulated and excreted a mixture of alpha- and beta-isopropylmalic acids.

Alpha-isopropylmalic acid is reported by Mikami et al., Agr. Biol. Chem. 34 (6), 977–9 (1970) to be a plant growth regulator. Japanese Pat. No. 70,032,919 of Oct. 23, 1970 (Chem. Abstr. 75, 31511v, 1971) describes its use for improving the flavor of tobacco. Its use as an intermediate for preparation of the tobacco flavor modifiers 2-isopropyl-4,4-dimethyl-5-methylene-2-cyclopenten-1-one and 2,5-diisopropyl-2-cylcopenten-1-one by dry distillation is disclosed in Japanese Kokai 77,113,945, published Sept. 24, 1977 (Chem. Abstr. 88, 62045u, 1978). German Offenlegungsschrift No. 2,922,222, published Dec. 13, 1979 (Chem. Abstr. 92, 152039g, 1980) describes its use and that of its sodium and ammonium salts as setting retardants for gypsum.

SUMMARY OF THE INVENTION

The present invention provides a fermentation process for producing alpha-isopropylmalic acid in substantially greater amounts than is produced by known microorganisms; and an improved process for recovering alpha-isopropylmalic acid from fermentation broths containing it.

The fermentation process comprises cultivating a new strain of *Yarrowia lipolytica*, ATCC 20628, which strain is auxotrophic for L-leucine, under submerged aerobic conditions in an aqueous nutrient medium containing assimilable sources of carbon, nitrogen, L-leucine and inorganic salts until a substantial amount of alpha-isopropylmalic acid accumulates in the medium.

The improved process for recovering alpha-isopropylmalic acid from fermentation broths containing the same comprises clarification and acidification of the broths followed by extraction thereof with methyl ethyl ketone.

The process of this invention achieves a broth potency 10 fold higher than that of any published procedure and the combined fermentation/recovery steps afford a 30 fold greater yield than do the said procedures.

DETAILED DESCRIPTION OF THE INVENTION

The fermentation process of this invention for producing exclusively alpha-isopropylmalic acid comprises cultivating a new strain of *Y. lipolytica* under aerobic conditions in an aqueous nutrient medium having an initial pH of about 6.0–7.0, preferably a pH of about 6.0–6.5. This new strain has been deposited in the American Type Culture Collection, Rockville, Md., a recognized depository affording permanence of the deposit and ready accessibility thereto by the public if a patent is granted on this application. This microorganism was given the designation *Yarrowia lipolytica* ATCC 20628. Access to the microorganism is available during pendency of this application to one determined by the Commissioner of the United States Patent and Trademark Office to be entitled thereto under 37 CFR 1.14 and 35 USC 122. All restrictions on the availability to the public of the microorganism deposited will be irrevocably removed upon granting of the patent.

The novel culture *Y. lipolytica* ATCC 20628 is identified in the Pfizer Inc. Culture Collection as PC 30781. Taxonomic studies (see below) of the culture were conducted by J. R. DeZeeuw and I. Stasko as recommended by Lodder in "The Yeasts", second edition, N. Holland Publishing Co., Amsterdam, 1970, except that all chemically defined media included 149 mg/liter of L-leucine ethyl ester hydrochloride as an amino acid supplement.

|  | Strain CBS 599[1] | Strain ATCC 20628 |
| --- | --- | --- |
| Cell Shape | ovoid | ovoid |
| Average Cell Size (microns) | 3.1 × 8.3 | 3.2 × 6.8 |
| Reproduction | budding | budding |
| Dalmau Plate Culture | Pseudo- and true mycelia prominent. Blastospores present, mostly as singles in pleural positions. | Pseudo- and true mycelia prominent. Blastospores present, mostly as singles in pleural positions. |
| Carotenoid Pigmentation | None | None |
| Nitrate Assimilation | − | − |
| Glucose Fermentation | − | − |
| Assimilation of Carbon Compounds |  |  |
| L-Arabinose | − | − |
| Cellobiose | − | − |
| Erythritol | + | + |
| D-Galactose | − | − |
| D-Glucose | + | + |

-continued

| | Strain CBS 599[1] | Strain ATCC 20628 |
|---|---|---|
| Inositol | − | − |
| Lactose | − | − |
| Maltose | − | − |
| D-Mannitol | + | + |
| Melibiose | − | − |
| Sucrose | − | − |
| Trehalose | − | − |
| D-Xylose | − | − |

[1]CBS 599 is the type culture for the species *Candida lipolytica*. [Also known as *Saccharomycopsis lipolytica*; now classified as *Yarrowia lipolytica* (Wickerham et al.) by van der Walt and von Arx, Antonie van Leeuwenhoek 46, 517-521, 1980].

Neither strain showed any growth at 37° C., but showed good growth at 28° C. in a basal medium comprising 6.7 g/liter of Bacto-yeast nitrogen base, 200 mcg/liter of thiamine hydrochloride, 149 mg/liter of L-leucine ethyl ester hydrochloride and 5.0 g/liter of D-glucose. Each strain requires thiamine for growth; and each assimilates ammonium sulfate and urea.

On the basis of its taxonomy compared to that of *C. lipolytica* CBS 599, PC 30781, ATCC 20628 is a strain of *Y. lipolytica*.

The aqueous nutrient medium must contain assimilable sources of carbon, nitrogen, L-leucine and inorganic salts. Representative carbon sources are a carbohydrate such as D-glucose, glycerol, D-mannitol, corn starch hydrolyzate, enzymatically hydrolyzed corn flour and enzymatically hydrolyzed corn meal; and fats and oils, illustrative of which are white grease and corn oil; n-paraffins such as n-hexadecane and n-paraffin mixture ($C_{12-16}$ range, available from Exxon Chemical Co., Baytown, Tex.). Preferred carbon sources are D-glucose, corn starch hydrolyzate and corn flour hydrolyzate since, for a given level of said carbon sources calculated in terms of their glucose equivalency, they tend to afford optimum yields of alpha-isopropylmalic acid. The carbon source is generally used at a level of from about 80 to 100 g/liter, calculated on the basis of glucose content or equivalency.

Suitable sources of nitrogen are soy bean hydrolyzate, enzymatic digest of casein, yeast extract, urea, ammonium sulfate, corn steep liquor, amino acids and peptones. A source of growth substances, such as distiller's solubles, yeast extract, molasses extract residues, as well as mineral salts such as sodium chloride, potassium chloride, monobasic potassium phosphate, magnesium sulfate, calcium carbonate (which also serves as buffer), and trace minerals such as zinc, iron and copper are beneficial to growth of the microorganism. Additionally, certain vitamins such as thiamine, usually as the hydrochloride salt, is required for proper growth of the microorganism.

An essential component of the medium is a source of L-leucine. The L-leucine can be added as such or in the form of a precursor; i.e., a substance which is converted to L-leucine during the fermentation. Representative L-leucine precursors are leucine containing peptides or protein hydrolysates, e.g. soybean meal. Concentrations of L-leucine or precursors thereof, calculated on the basis of their L-leucine equivalence, of from about 0.2 to 5.0 g/liter of medium are especially useful in achieving optimum production of alpha-isopropylmalic acid. The preferred concentration of L-leucine, or a precursor thereof, is from 0.5 to 1.0 g/liter calculated as L-leucine. The favored L-leucine source is L-leucine itself.

As noted above, the fermentation is an aerobic fermentation. While any form of aerobic incubation is satisfactory, controlled aeration is preferred, as for example, by agitating the medium under air, or by sparging of air through the medium. The microorganism is cultivated at a temperature of from about 24°-30° C., and preferably at 28° C.

Antifoam agents such as silicones, vegetable oils and non-ionic surfactants, especially the block polymers of ethylene oxide and propylene oxide, are generally added to the fermentation medium to control foaming.

The inoculum required for the fermentation is obtained by removing the vegetative cells from slants incubated with a culture of *Y. lipolytica* ATCC 20628. A solid medium suitable for initial growth on slants is the following:

| | |
|---|---|
| Bacto-peptone | 25.0 g/liter |
| Bacto-nutrient broth | 8.0 g/liter |
| Bacto-yeast extract | 5.0 g/liter |
| D-glucose | 5.0 g/liter |
| Gentamicin | 50.0 mg/liter |
| Agar | 20.0 g/liter |

The slants are inoculated with the *Y. lipolytica* and incubated for 24 hours at 28° C. The vegetative cells produced are removed and used to inoculate tubes or shake flasks containing the above-described medium, but without the agar. Incubation is carried out for 22 hours at 28° C. on a gyrotary shaker. The vegetative cells thus produced are used to inoculate larger containers, e.g. four liter fermentation pots, containing an appropriate medium for growth, such as exemplified herein. Incubation is carried out at from 24°-28° C. for up to nine days using an aeration rate of 2 liters/minute/pot. Sterility is maintained at all times.

Upon completion of the fermentation, the alpha-isopropylmalic acid is recovered by acidifying the broth to pH of about 1.0-2.0, preferably to pH 1.5 by addition of a mineral acid, e.g., sulfuric or hydrochloric acid. The acidified broth is stirred for one to two hours and is then filtered. The clarified broth is then extracted with methyl ethyl ketone and the alpha-isopropylmalic acid obtained by evaporation. Additional product can be recovered from the raffinate by extraction as before.

The fermentation broth need not be clarified prior to recovery of the alpha-isopropylmalic acid. However, clarification prior to extraction serves to simplify the recovery process.

Other water immiscible solvents such as methyl isobutyl ketone, n-butanol, isobutanol, ethyl acetate and, of course, ether can be used. However, methyl ethyl ketone is the peferred solvent for reasons of safety in handling and the ease with which crystalline alpha-isopropylmalic acid can be obtained by concentrating the extracts.

It is to be understood that the present invention is not limited to use of the aforesaid organism which fully answers the above description, and which is given only for illustrative purposes. It is especially desired and intended to include the use of naturally occurring or artificially induced mutants and/or variants, such as those which can be produced from the described organism, by various means, including x-radiation, ultraviolet radiation, treatment with nitrogen mustards, and the like.

We wish also to include any organism, regardless of its appearance or physiological behavior, that may be developed by means of transformation, transduction, genetic recombination or some other genetical procedure, using a nucleic acid or an equivalent material from the herein described species, whereby it has acquired the ability to produce the elaboration product here described or to carry on the biochemical change here described.

EXAMPLE 1

Production and Recovery of Alpha-Isopropylmalic Acid D-Glucose Carbon Source

Culture Preparation

The solid from a standard freeze-dry tube of *Y. lipolytica* ATCC 20628 was suspended in 1.0 ml of sterile water. Then, slants comprising 17 ml per 25×150 mm tube of medium A solidified with Bacto-agar (20 g/liter) were inoculated with 0.2 ml portions of the suspension.

| Medium A | |
|---|---|
| Bacto-peptone | 25.0 g/liter |
| Bacto-nutrient broth | 8.0 g/liter |
| Bacto-yeast extract | 5.0 g/liter |
| D-glucose | 5.0 g/liter |
| Gentamicin | 0.05 g/liter |

The pH of the medium was 6.8–6.9. The bulk was sterilized by autoclaving for 30 minutes at 15 psi (1.02 atmospheres). The glucose was sterilized separately.

The slants were incubated for 24 hours at 28° C. before use in preparing the inoculum.

Preparation of Inoculum

A slant prepared as described above was washed with 20 ml of sterile distilled water. The resulting cell suspension was used to inoculate 70 tubes (25×150 mm) containing 10 ml of medium A per tube at the level of 0.2 ml of cell suspension per tube. The tubes were cotton-plugged and incubated for 22 hours at 28° C. on a gyrotary shaker having a 2.54 cm (1 inch) stroke at 200 revolutions per minute (rpm) and angled at 30° C. The growth from the tubes was then pooled.

Fermentation

The following bulk medium was made up:

| | | |
|---|---|---|
| $(NH_4)_2SO_4$ | 4.0 | g/liter |
| Corn steep liquor | 5.0 | g/liter |
| $KH_2PO_4$ | 0.5 | g/liter |
| $MgSO_4.7H_2O$ | 0.25 | g/liter |
| $CaCO_3$ (marble white) | 15.0 | g/liter |
| L-leucine | 1.0 | g/liter |
| Thiamine.HCl | 400.0 | mcg/liter |
| Tap water | to 80% | volume |
| (pH = 6.1–6.2) | | |

All ingredients except D-glucose were made up to 80% of final volume. The bulk medium (1600 ml) was added to each of 8 stirred four liter fermentation pots and sterilized at 15 psi (1.02 atmospheres) for 30 minutes. D-glucose as a 50% (w/v) solution, sterilized by autoclaving at 15 psi (1.02 atmospheres) for 30 minutes, was then added to each pot at the rate of 400 ml/pot. Pluronic L-81 [a liquid non-ionic surfactant of the poly-(oxypropylene)poly(oxyethylene) type having an average molecular weight of 2750; available from BASF Wyandotte], 1.0 ml/pot (sterilized as above) was added as antifoaming agent.

Each pot was inoculated with 80 ml of pooled inoculum and incubated for nine days at 26° C. with stirring at 1750 rpm and aeration at 2 liters/minute/pot.

Clarification

The broth from the fermentation pots was combined (pH 4.13), adjusted to pH 1.5 by addition of concentrated sulfuric acid, and then stirred for one hour. It was vacuum filtered to afford 11.55 liters of clarified broth (50 ml removed for assay showed an alpha-isopropylmalic acid level of 42.8 mg/ml; for a total of 494.3 g).

Recovery of Alpha-Isopropylmalic Acid

The clarified broth (11.5 liters) was extracted with an equal volume of methyl ethyl ketone and the extract stripped of solvent under reduced pressure in a rotary evaporator partially immersed in a water bath at 40°–41° C. The (first) raffinate, pH 1.77, was adjusted to pH 1.5 by addition of sulfuric acid, then vacuum filtered. The filtrate was extracted with an equal volume of methyl ethyl ketone saturated with water and the solvent stripped as described above. The second raffinate (pH 1.57) was adjusted to pH 1.5 by means of sulfuric acid and extracted with an equal volume of methyl ethyl ketone saturated with water. The extract was stripped of solvent as were the two earlier extracts. The concentrated extracts were combined (total volume 1800 ml) and decolorized by treatment with 13.0 g of activated charcoal. The clear amber solution obtained was concentrated under reduced pressure at 70° C. to a partially solid mass. It was transferred to a one liter beaker and sufficient water added at 85° C. to effect solution. The solution was stirred and allowed to cool until room temperature was reached. After standing at room temperature overnight, the crystalline alpha-isopropylmalic acid was separated by vacuum filtration and the filter cake washed with a small volume of cold water. The crystals were dried overnight in a steam heated cabinet to give 381.9 g of off-white crystals.

The combined mother liquor and wash water was concentrated in vacuo at 70° C. and the concentrate worked up as before to give 62.9 g of light brown crystals. The combined mother liquor and wash water was concentrated in vacuo as before to give a viscous liquid which did not crystallize. It assayed for 24.8 g of alpha-isopropylmalic acid. Total amount of alpha-isopropylmalic acid recovered from the 11.5 liters of clarified broth=469.6 g.

The combined raffinates assayed for 1.38 mg/ml of alpha-isopropylmalic acid, for a total of 17.9 g alpha-isopropylmalic acid.

Identity of the product as alpha-isopropylmalic acid [S(−)-2-hydroxy-2-(1-methylethyl)butanedioic acid] was established by comparison of its m.p, IR, $^{13}C$-NMR and $^{1}H$-NMR with those of alpha-isopropylmalic acid produced by *Neurospora crassa*.

EXAMPLE 2

Production and Recovery of Alpha-Isopropylmalic Acid-Corn Flour Carbon Source

Fermentation

Inoculum prepared as described in Example 1 was fermented in fermentation pots (4 liter size) using a medium having the following composition.

| | |
|---|---|
| Crude corn syrup (having 263 mg D-glucose/g) | 380.0 g/liter |
| Corn steep liquor | 5.0 g/liter |
| $(NH_4)_2SO_4$ | 4.0 g/liter |
| $KH_2PO_4$ | 0.5 g/liter |
| $MgSO_4.7H_2O$ | 0.25 g/liter |
| $CaCO_3$ (marble white) | 15.0 g/liter |
| L-leucine | 1.0 g/liter |

| | |
|---|---|
| -continued | |
| Thiamine.HCl | 400.0 mcg/liter |
| Pluronic L-81 | 0.5 ml/liter |
| Tap water | |
| (pH = 6.1–6.2) | |

Each of 8 four liter pots was charged with 760 g crude corn syrup made up to 1000 ml, adjusted to pH 6.1 with potassium hydroxide, with tap water. Calcium carbonate (30.0 g) and 500 ml of tap water were added and the mixture sterilized by autoclaving at 15 psi (1.02 atmospheres) for 30 minutes. The remaining ingredients (except Pluronic L-81) were made up to 25% of final volume, 500 ml portions thereof sterilized separately at 15 psi (1.02 atmospheres) for 30 minutes, and added to each pot. The Pluronic L-81 was sterilized as above and 1 ml added to each pot.

Each pot was incubated with 80 ml of inoculum according to the procedure of Example 1.

Clarification and Recovery

The broth from 4 pots was clarified according to the procedure of Example 1 to give 6.2 liters of clarified broth which assayed 39.7 g of alpha-isopropylmalic acid/liter.

Recovery according to the procedure of Example 1 afforded 238.5 g of alpha-isopropylmalic acid from 6.19 liters of clarified broth. The combined raffinates (8500 ml) assayed for 0.98 mg/ml, equivalent to 8.3 g alpha-isopropylmalic acid in the raffinate.

Assay Procedure (An adaptation of the procedure of Calvo et al., Anal. Biochem. 28, 164–181, 1969)

For Broths Containing Alpha-IPM:

Ten ml of whole broth was adjusted to pH 1.5 with dilute sulfuric acid and then sufficient distilled water added to increase the volume to 50 ml. A portion (10–20 ml) of the acidified and diluted whole broth solution was clarified by centrifugation and 5 ml of the clarified solution mixed with 5 ml of buffer (0.2 M $Na_2SO_4$ adjusted to pH 1.5 with 0.2 M $H_2SO_4$).

Four ml of the buffered solution was then charged to a ClinElut Disposable Extraction Column (Fisher Scientific Company, Pittsburgh, PA, Catalog No. 1005). The sample was allowed three minutes to adsorb on the column and then 8 ml of methyl ethyl ketone (MEK) passed through the column by gravity flow. The eluate was collected in a 25 ml volumetric flask and the elution repeated twice more with 8 ml volumes of MEK. The volume of the combined eluates was then brought to 25 ml by addition of MEK.

A 1.0 ml sample of eluate was evaporated to dryness in a tube using a nitrogen stream and a 65° C. heating block. To the residue was added 0.4 ml of 95% concentrated $H_2SO_4$, the tube incubated in a 30° C. water bath for 20 minutes and then chilled. Then 0.25 ml of cold 1.84 M aqueous resorcinol solution was added, the mixture incubated in a 30° C. water bath for 30 minutes and then 9.35 ml water added. A 0.1 ml portion of the resulting solution was diluted to 10 ml with pH 10 buffer (0.1 M $H_3BO_3$-0.4 M $Na_2CO_3$) and the fluorescense determined using an Aminco-Bowman instrument, using settings for maximum fluorescense: 360 nm for excitation and 453 nm for emission, and the values compared with those of a standard.

We claim:

1. A process for producing alpha-isopropylmalic acid which comprises cultivating *Y. lipolytica* ATCC 20628 in an aqueous nutrient medium having an initial pH of about 6.0–7.0 and containing assimilable sources of carbon, nitrogen, L-leucine and inorganic salts under submerged aerobic fermentation conditions until a substantial amount of alpha-isopropylmalic acid accumulates in the medium.

2. A process according to claim 1 wherein the alpha-isopropylmalic acid is recovered from the medium.

3. A process according to claim 2 wherein the source of L-leucine is L-leucine itself.

4. A process according to claim 2 wherein the carbon source is D-glucose.

5. A process according to claim 2 wherein the carbon source is enzymatically hydrolyzed corn flour.

6. A process according to claim 4 or 5 wherein the L-leucine source is L-leucine itself.

7. A culture consisting essentially of *Yarrowia lipolytica* ATCC 20628, said culture being capable of producing alpha-isopropylmalic acid in recoverable quantity upon submerged aerobic fermentation.

8. The culture of claim 7 in freeze dried form.

* * * * *